(12) United States Patent
D'Souza et al.

(10) Patent No.: US 7,120,925 B2
(45) Date of Patent: Oct. 10, 2006

(54) SYSTEM AND METHOD FOR DISPLAYING EDITORIAL CONTENT THROUGH TELEVISION NAVIGATION CONTROLS AND ELECTRONIC PROGRAM GUIDES

(75) Inventors: Errol D'Souza, Sicklerville, NJ (US); Francis D. Palazzo, Dresher, PA (US); Bruce Plotnick, Jamison, PA (US)

(73) Assignee: Sedna Patent Services, LLC, Philadelphia, PA (US)

( * ) Notice: Subject to any disclaimer, the term of this patent is extended or adjusted under 35 U.S.C. 154(b) by 52 days.

(21) Appl. No.: 10/022,650

(22) Filed: Dec. 17, 2001

(65) Prior Publication Data

US 2006/0117348 A1  Jun. 1, 2006

(51) Int. Cl.
*H04N 7/173* (2006.01)

(52) U.S. Cl. .................... 725/100; 725/41; 725/50; 725/54; 725/52; 725/131; 725/139; 725/151

(58) Field of Classification Search .......... 725/40, 725/41, 42, 43, 51, 52, 54, 56, 57, 32–36, 725/87, 90, 93–96, 98, 109, 110, 112, 132, 725/140, 152

See application file for complete search history.

(56) References Cited

U.S. PATENT DOCUMENTS

| 4,532,554 | A | * | 7/1985 | Skala ........................ 358/434 |
| 4,605,973 | A | * | 8/1986 | Von Kohorn ................. 386/54 |
| 5,657,072 | A | * | 8/1997 | Aristides et al. .............. 725/46 |
| 5,659,350 | A | * | 8/1997 | Hendricks et al. .......... 725/116 |
| 5,678,012 | A | * | 10/1997 | Kimmich et al. ............. 725/37 |
| 5,751,282 | A | * | 5/1998 | Girard et al. ............... 345/721 |
| 5,907,323 | A | * | 5/1999 | Lawler et al. ................ 725/41 |
| 6,002,394 | A | * | 12/1999 | Schein et al. ................. 725/39 |
| 6,005,631 | A | * | 12/1999 | Anderson et al. ............. 725/53 |
| 6,025,837 | A | * | 2/2000 | Matthews et al. .......... 345/721 |
| 6,177,931 | B1 | * | 1/2001 | Alexander et al. ........... 725/52 |
| 6,208,384 | B1 | * | 3/2001 | Schultheiss ................ 348/552 |
| 6,263,501 | B1 | * | 7/2001 | Schein et al. ................. 725/39 |

\* cited by examiner

*Primary Examiner*—Jason Salce
(74) *Attorney, Agent, or Firm*—Patterson & Sheridan, LLP (57) ABSTRACT

A system and method for presenting advanced editorial content items to subscribers in a distribution network. The method comprises presenting an electronic program guide comprised of data representing program availability on a broadcast distribution network and a selectable editorial content control to present an editorial content index page. An editorial content index page is presented on a display device within the context of the electric program guide in response to selecting the editorial content control, the editorial content index page comprising one or more links or pointers, such as hyperlinks, to editorial content items. A user selects a pointer to an editorial content item from the set of pointers and the editorial content item is presented on the display device.

16 Claims, 5 Drawing Sheets

SYSTEM AND METHOD FOR DISPLAYING EDITORIAL CONTENT THROUGH TELEVISION NAVIGATION CONTROLS AND ELECTRONIC PROGRAM GUIDES

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

RELATED APPLICATION

This application is related to commonly owned provisional application entitled "SYSTEM AND METHOD FOR DIGITAL TV NAVIGATOR AND EPG", application Ser. No. 60/340,329, said application filed on Dec. 13, 2001 and hereby incorporated by reference in its entirety.

BACKGROUND OF THE INVENTION

The invention disclosed herein relates generally to rich media content delivery systems. More particularly, the present invention relates to a system and method for providing editorial content comprising rich media through television navigation controls and electronic program guides.

Various audio/video navigation and electronic program guide systems are known to those skilled in the art. These systems typically provide some degree of interactive functionality whereby advanced navigation features are made available to a user of such a system. For example, electronic program guides are provided whereby a user may explore programming available at a variety of future times. Likewise, advanced information may be provided to users as they navigate among the channels that comprise the available programming.

Currently deployed or developed cable systems provide functionality that allows for brief textual descriptions to be accessed through the use of an input device. These brief textual descriptions typically comprise a summary of the program, rating, start and end times, and other miscellaneous programming data. These current systems, however, do not provide access to rich media editorial content items. Furthermore, these brief textual descriptions do not provide for interactive functionality or contemplate executing interactive code to better interface with the user.

There is thus a need for a system and method whereby a variety of editorial content items comprised of rich media may be viewed within a set of television navigation controls or an electronic program guide.

BRIEF SUMMARY OF THE INVENTION

The instant invention presents a system and method for presenting advanced editorial content items to subscribers in a distribution network. The method of the present invention comprises presenting an electronic program guide comprised of data representing program availability on a distribution network and a editorial content control to present an editorial content index page. An editorial content index page is presented on a display device within the context of the electric program guide in response to selecting the editorial content control, the editorial content index page comprising one or more links, such as pointers or hyperlinks, to editorial content items. A user selects a pointer to an editorial content item from the set of pointers and the editorial content item is presented on the display device. The editorial content item comprises text data, video data, interactive data and various combinations thereof. The interactive code may comprise java program code, flash program code, or any other interactive program code know to those skilled in the art.

According to another embodiment of the invention, presenting editorial content items on a display device comprises presenting an electronic program guide comprised of data representing program availability on a distribution network and a editorial content control to present an editorial content index page. An editorial content index page is displayed on a display device within the context of the electric program guide in response to selecting the editorial content control, the editorial content index page may comprise one or more pointers to editorial content items. A user selects a pointer to an editorial content item from the set of pointers and presents the editorial content item on the display device.

The method may comprise receiving the editorial content index page and one or more editorial content items at a client device on a periodic basis. The editorial content index page and one or more editorial content items may be received at a client device through a carousel distribution system distributing data in a carousel fashion. The method also comprises exiting the editorial content index page and presenting the electronic program guide. Alternatively, the editorial content index page may be exited and a channel viewed by the user before the electronic program guide is displayed.

According to other embodiments of the invention, a method for presenting editorial content items on a display device comprises presenting a surf guide configured to display limited program information and an editorial content control to present an editorial content index page. The editorial content index page is presented within the context of the electronic program guide in response to selecting the editorial content control, the editorial content index page comprising one or more pointers to editorial content items. The user selects a pointer to an editorial content item from the set of pointers and the editorial content item is displayed on the display device. The method may comprise exiting the editorial content index page and presenting a surf guide configured to display limited program information and the editorial content control. Alternatively, the method may comprise exiting the editorial content index page and presenting a channel viewed by the user before the step of displaying the surf guide was conducted.

Embodiments of the invention may be embodied in computer readable media comprising program code, the program code capable of being executed by a microprocessor, the program code comprising a method for presenting editorial content items on a display device. The method comprises presenting an electronic program guide comprised of data representing program availability on a distribution network and a editorial content control to present an editorial content index page. An editorial content index page is presented on a display device within the context of the electric program guide in response to selecting the editorial content control, the editorial content index page comprising one or more pointers to editorial content items. A user selects a pointer to an editorial content item from the set of pointers and the editorial content item is presented on the display device.

The system of the present invention for presenting editorial content items on a display device comprises one or more editorial content items comprising, audio, video, interactive data and combinations thereof, as well as an editorial content index comprising pointers to the one or more editorial content items. The system also comprises presentation software operative to generate and present on a display device navigational controls and an electronic program guide. The presentation software is further operative to display the editorial content index within the context of the electronic program guide and render the one or more editorial content items on the display device.

BRIEF DESCRIPTION OF THE DRAWINGS

The invention is illustrated in the figures of the accompanying drawings which are meant to be exemplary and not limiting, in which like references are intended to refer to like or corresponding parts, and in which.

DETAILED DESCRIPTION OF THE PREFERRED EMBODIMENTS

Figure 1:
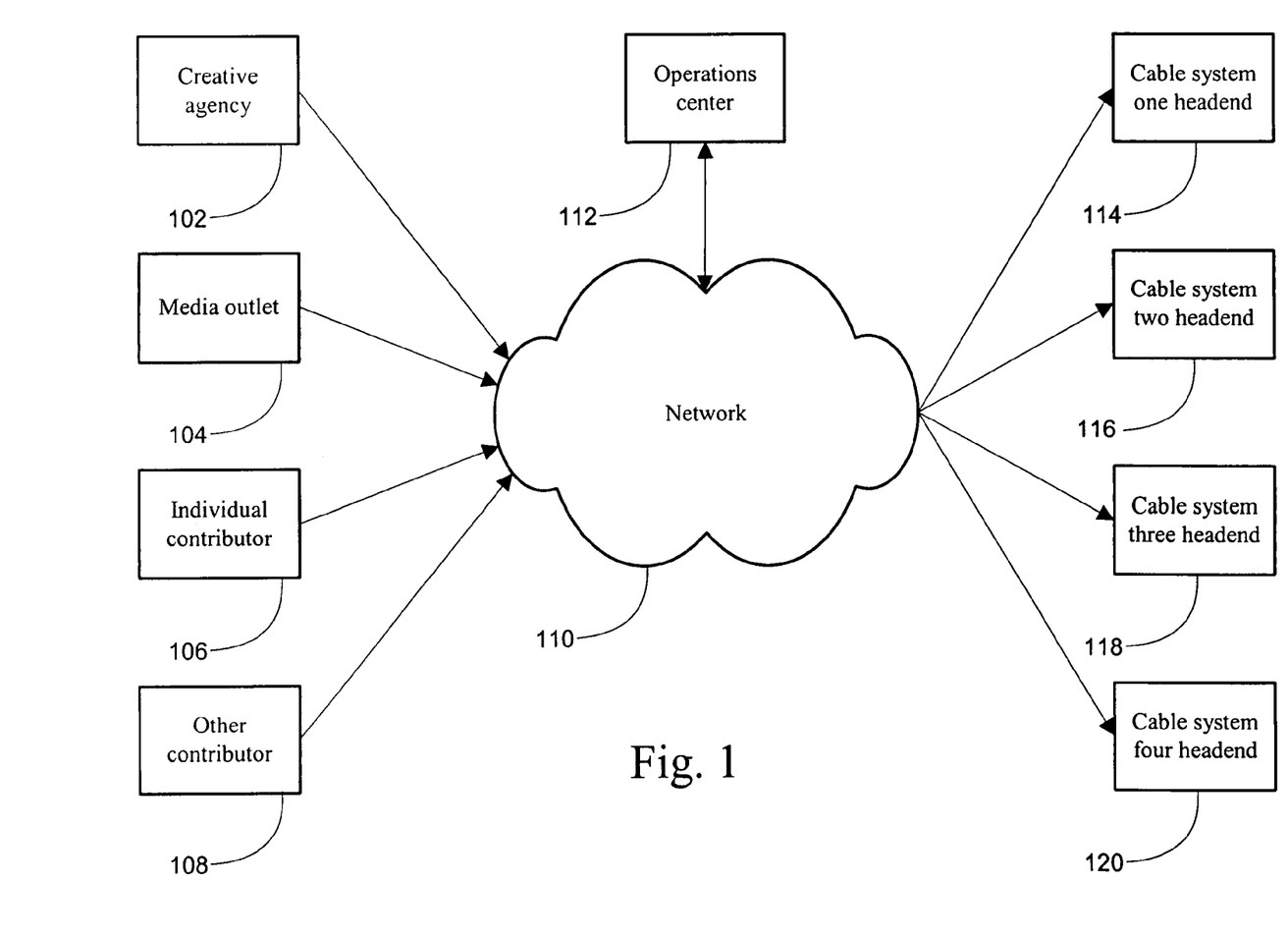
FIG. 1 is a block diagram presenting a configuration of hardware components for distributing editorial content to a variety of distribution systems according to one embodiment of the present invention.

With reference to FIG. 1, a block diagram illustrating part of an editorial content distribution network is presented. The notion of editorial content is a broad concept encompassing a wide variety of opinions and facts regarding programming, typically entertainment and other audio/video information, distributed over a distribution network such as a cable television network. Editorial content, therefore, may be supplied by a diverse assortment of editorial content producers. One such editorial content producer is a creative agency 102, for example, an advertising agency. Another exemplary editorial content producer is a media outlet 104 such as a web site or network television station, e.g., MSNBC and NBC, respectively. The term editorial content likewise includes individual editorial content producers 106, for example, individuals contributing their opinions to message boards and other types of bulletin board systems, as well as other types and sources of editorial content 108, e.g., freelance writers. In addition to a wide variety of sources, editorial content includes a variety of disparate digital media types including, but not limited to, text, graphics, audio, video, and interactive content. Combinations of these and other media types fall within the definition of editorial content as contemplated by the various embodiments of the invention.

Editorial content producers are provided with a connection to one or more networks 110 with the capacity to transmit data. For example, the connection may be a broadband or other local area network connection the Internet. Alternatively, the connection may be a dial-up connection to the Internet or other wide area data network via the public switched telephone network (PSTN). The editorial content providers, 102, 104, 106, 108 transmit editorial content via the network 110 to an operations center 112, which is responsible for coordinating delivery of guide and other data to subscribing cables systems 114, 116, 118, and 120. The operations center 112 also transforms the received editorial content into a standard format for each particular media type in order ensure that all editorial content delivered to subscribing cable systems 114, 116, 118, and 120 is uniform. The editorial content is preferably transmitted to the subscribing cable systems 114, 116, 118, and 120 via the same link used to deliver guide and other data, e.g., the same network 110, although an alternate transmission system may be used.

Figure 2:
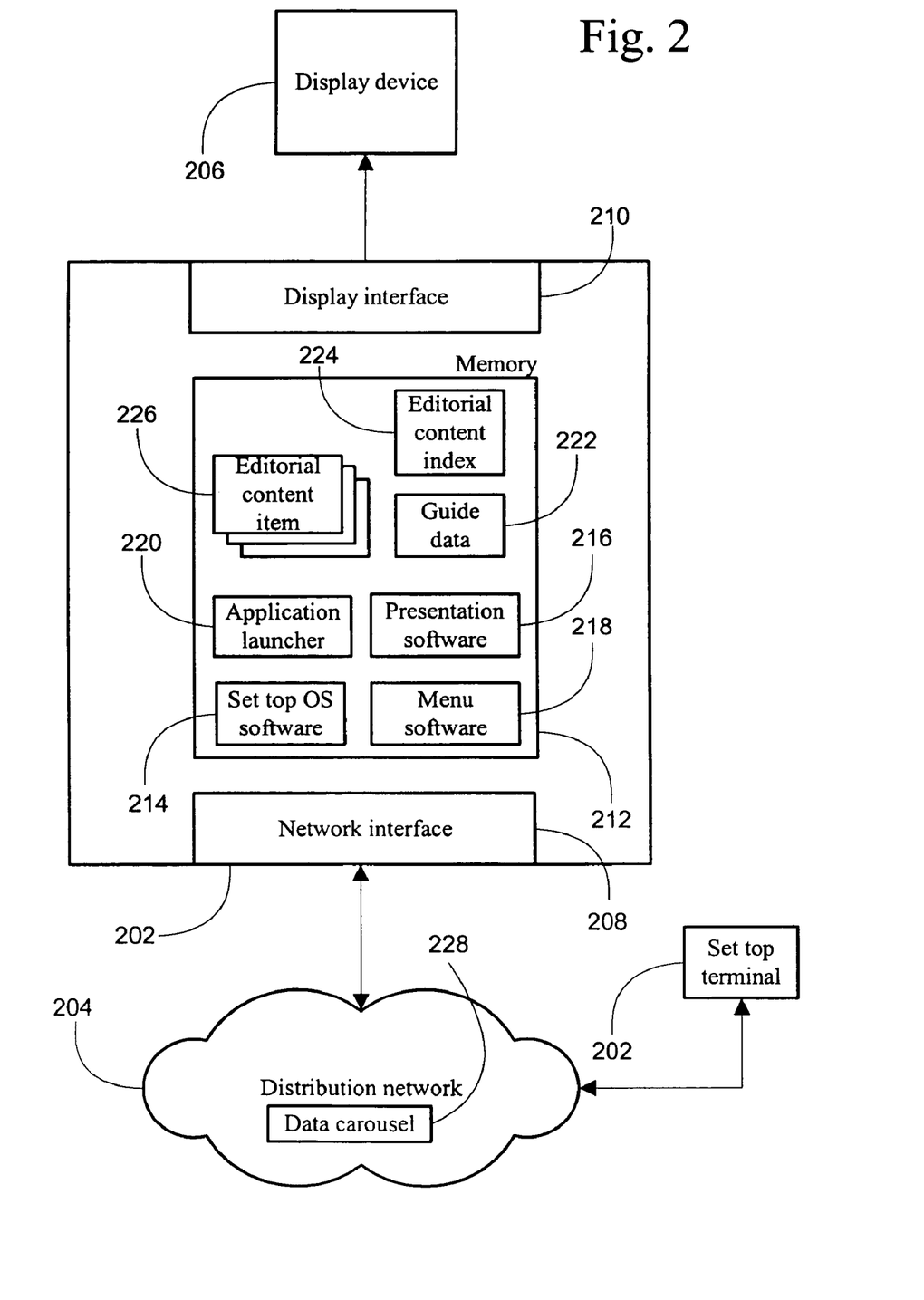
FIG. 2 is a block diagram presenting a configuration of hardware and software components used to present editorial content according to one embodiment of the present invention.

The editorial content, guide data, and other data are received by the subscribing cable systems 114, 116, 118, and 120, where it is prepared for delivery to set top terminals and other digital devices under the control of subscribing customers. FIG. 2 presents a block diagram illustrating one embodiment of the hardware and software components used to deliver and process editorial content, guide data, and other data for presentation to a user connected to a distribution network. A distribution network 204 is used to distribute digital and analog audio and video data to one or more subscribing customers' set top terminals 202. According to some embodiments, the distribution network comprises a coaxial infrastructure, a fiber optic infrastructure, a hybrid fiber-coax infrastructure, a wireless infrastructure, or a combination of these and other delivery technologies well known to those skilled in the art. Audio and video data is transported across the distribution network 204 to a subscriber's set top terminal 202 where the data is received across the terminal's network interface 208. Exemplary set top terminals include the DCT1000, DCT1200 and DCT2000 manufactured by General Instruments, or any other set top terminal or receiver as are well known to those skilled in the art.

Software programs 214, 216, 218, and 220 stored in memory 212 on the set top terminal 202 are used to decode and present the audio, video and other data received from the distribution network 204 on a display device 206. Software components used to present audio and video data, as well as advanced navigation and EPG features of the present invention include set top OS software 214, presentation software 216, menu software 218, and application launcher software 220. Set top operating system software 214 is used to provide the core operating system functionality of the set top terminal 202, such as basic input/output and other low level functions. The OS software 214 also provides a framework for executing application program code, e.g., presentation 216, menu 218, and application launcher 220 software.

The set top presentation software 216 is used to present navigation tools and an electronic program guide (EPG) to the set top terminal user. The presentation software 216 fetches and displays scripts, which are pages of content, such as formatted program guide data, which may be used to construct an electronic program guide. The scripts are retrieved from a data carousel 228 located on the distribution network 228 in response to user commands. As a user manipulates an input device, e.g., remote control or wireless keyboard, to request additional program guide content, the presentation software 216 fetches the appropriate script from the data carousel 228 for presentation on the display device 206. The presentation software 216 may also be configured to display the EPG along with audio and video data being transmitted on the last channel viewed before activating the EPG.

The presentation software 216 also presents a user interface control within the EPG to load and display an editorial content index 224. The control is optionally presented within each script comprising the EPG that is fetched by the presentation software 216 from the data carousel 228. According to embodiments of the invention, the presentation software 216 retrieves the index from the data carousel 228 as a formatted data page in response to the user selecting the control to load the index. Alternatively, the index 224 is transmitted to the terminal on a periodic basis as part of the set of guide data 220 utilized by the presentation software to construct a surf guide, which is explained in greater detail herein. The index 224 comprises, but is not limited to, selectable entries linking to each editorial content item 226 in memory 212 and is preferably formatted similarly to other pages of the EPG.

In addition to EPG functionality, the presentation software 216 provides navigation tools in the form of a surf guide that is displayed to the user each time a channel is tuned. Advantageously, the surf guide may be overlaid on top of the currently tuned program for a predetermined or variable number of seconds. In keeping with some embodiments, data 222 for the surf guide generated by the presentation software 216 is retrieved from the distribution network 204 on a periodic basis, e.g., upon exceeding a time threshold after the set top power has been cycled on. This data is stored in the set top memory 212 as guide data 222, which is used to populate the displays generated by the presentation software.

The surf guide presents guide data 222 that comprises channel number and network identifier, program title, program start and end times, and other miscellaneous program data. According to some embodiments, the surf guide is presented in response to user selection of an appropriate control on the input device. The surf guide may be used in conjunction with directional controls located on the input device to step through the guide data 222. Using the surf guide, the user may view information regarding future or past programming on the channel currently being viewed or other channels that comprise the channel map for the subscriber's distribution system. Like the EPG, the presentation software 216 also presents a control within surf guide to load and display the editorial content index 224

Besides guide data 222, the set of data periodically retrieved from the distribution network 204 includes editorial content items 226. Alternatively, the editorial content items 226 may be placed in the data carousel 228 and accepted by set top terminals as is necessary. The editorial content items 226 may be comprised of a diverse combination of media types including text, graphics, audio, video, interactive content, as well as combinations thereof. Text content may be combined with graphics to create a review of a particular program or episode of a program. Interactive content may include program code, e.g., Flash or Java code, used to present combinations of text, graphics, audio and video on the display device 206, which the user may interact with through the use of an input device.

Menu software 218 is stored in the set top terminal's memory 112 and provides a menu-based interface for configuring the present system. Menu software 218 responds to commands provided by the user through the use of an input device. Through the menu interface provided by the menu software 218, a user is able to customize features of the operating system 214 and presentation software 216, as well as other software components resident on the set top terminal 202. For example, using the menu software 218, a user is capable of setting parental passwords, setting purchase passwords, and locking or unlocking channels. The menu software may also be used to generate lists of favorite channels, which may be activated and traversed by the user. Indeed, the menu software is constructed to allow configuration of all aspects of audio and video presentation as well as the full screen EPG and surf guides generated by the presentation software 216.

Also provided is an application launcher software module 120, which is responsible for launching other software and program code that the set top terminal requires to render certain types of editorial content items 226 or other content data that might be resident in the terminal's memory. A user interacts with the set top terminal presentation software 216, through the use of navigation tools such as the surf guide and the full screen electronic program guide, to access the editorial content index and associated editorial content items 226. When certain content items are selected, additional software is loaded in order to render the content. Accordingly, a video generator may be used to properly format content items for display on a television. For example, a Flash run time session must be instantiated when an editorial content item comprising an interactive piece of Flash code is to be rendered. The application launcher 220 comprises program code to instantiate required run time sessions or other supporting code.

As one skilled in the art should readily recognize, a variety of programming languages, paradigms, and tools may be used to create the software components of the present invention 214, 216, 218, and 220. These software components may be presented as a single, unified software component or, alternatively, broken into additional functionally targeted software components according to various embodiments of the invention. Furthermore, the data files presented herein 222, 224, 226 may be implemented utilizing any number and type of data structures including, but not limited to, tab delimited files, comma delimited files, tables within a relational database, objects within an object oriented database, or structures within a hybrid relational-object database.

Figure 3:
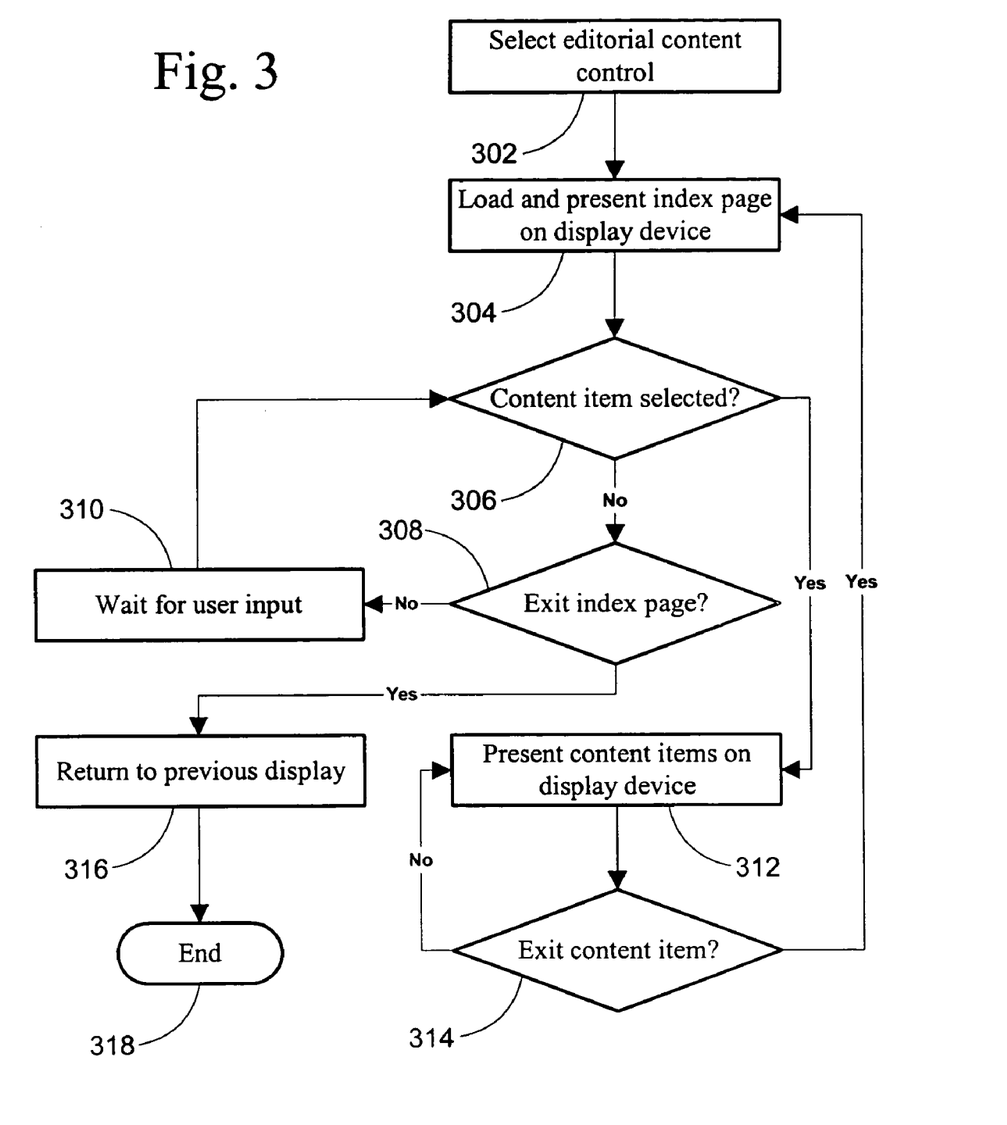
FIG. 3 is a flow diagram presenting a process for displaying editorial content according to one embodiment of the present invention.

One embodiment of a method for operating the system illustrated in FIG. 1 and two is presented in FIG. 3. Program flow begins when the user selects the editorial control presented through both the full screen EPG and navigational surf guide, step 302. The presentation software or other responsible software component comprising the system loads the editorial content index page and presents it on the display device, step 304. According to embodiments of the invention, a genre option is provided, which is available from all full screen EPG pages and menu screens, whereby selection of the option presents the index page. Likewise, the index page is activated from the surf guide when the genre filters are on the screen.

The index page is loaded and presented on the display device, step 304, and a check is performed by the presentation software to determine if a content item has been selected out of the set of content item links presented by the index page, step 306. Where the check returns false, a check is performed to ascertain whether the user has instructed the system to close the index page, step 308. Where the user has neither selected an editorial content item from the index nor issued a command to close the index page and return to the previous display, steps 306 and 308, program flow passes to step 310 where the system waits for user input. Alternatively, an additional step, which has not been pictured in the figure, may comprise trapping for commands to scroll the list of content items comprising the index page where the list is greater than the vertical or horizontal dimensions of the display area provided by the display device. The commands are trapped, causing the index to scroll accordingly on the display device, and program flow continues at step 310 where the presentation software waits for user input.

When the user selects a content item, step 306, the content item is presented on the display device, step 312. According to various embodiments of the invention, specific viewing applications or applets are launched by the application launcher software as is required to support the presentation of the editorial content item on the display device. The editorial content item may be displayed in place of the editorial content index page, within the context of the surf guide, within the context of the electronic program guide, or any other area of the display device alone or in conjunction with other display elements presented herein.

A check is performed to determine if the user has issued a command to exit the selected content item, step 314, typically after the entire editorial content item has been viewed. If the check returns false, the editorial content continues to be presented on the display device, step 312. Where the user issues a command to exit the currently displaying editorial content item, the editorial content index loads and the index is presented on the display device, step 304. Processing continues through decision gates 306 and 308. Where the user has issued a command to exit the editorial index page, step 308, the presentation software returns to the previous display, step 316. For example, the user may be returned to the full screen EPG or surf guide presented on the display device over the current program on the channel that the user was watching when the editorial guide was loaded. The process concludes at step 318.

Figure 4:
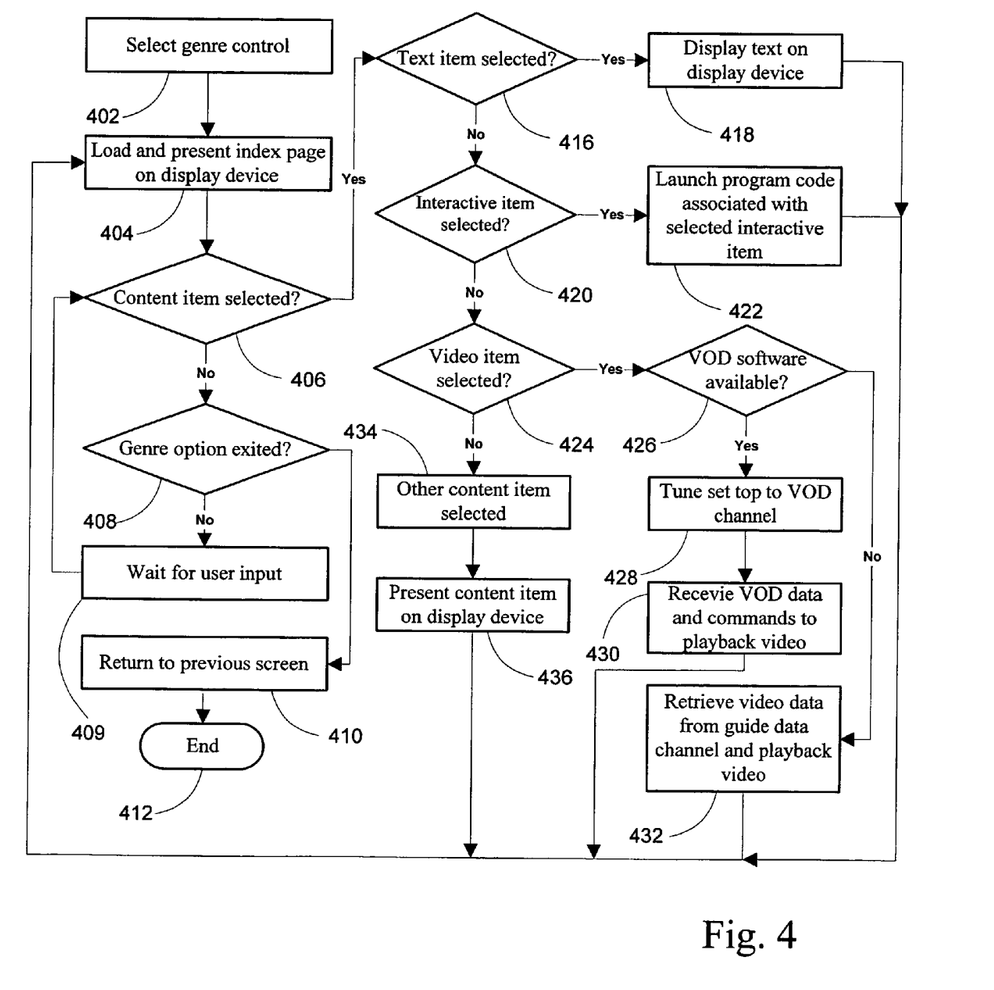
FIG. 4 is a flow diagram presenting a process for displaying editorial content according to another embodiment of the present invention.

Another embodiment of a process for displaying editorial content using the system presented in FIG. 2 is shown in FIG. 4. Program flow begins when the user selects the editorial control presented through either the full screen EPG and navigational surf guide, step 402. The presentation software or other responsible software component comprising the system loads the index page and presents it on the display device, step 404. According to embodiments of the invention, a genre option is provided, which is available from all full screen EPG pages and menu screens, whereby selection of the option presents the index page. Likewise, the index page is activated from the surf guide when the genre filters are on the screen.

The index page is loaded and presented on the display device, step 404, and a check is performed by the presentation software to determine if a content item has been selected out of the set of content item links presented by the index page, step 406. Where the check returns false, a check is performed to ascertain whether the user has instructed the system to close the editorial content index page, step 408. Where the user has neither selected a content item from the index nor issued a command to close the index page and return to the previous display, steps 406 and 408, program flow passes to step 409 where the system waits for user input. If the user instructs the editorial content index page to be closed, step 408, the presentation software returns to the previous display, step 410. For example, the user may be returned to the full screen EPG or surf guide presented on the display device over the current program on the channel that the user was watching when the editorial guide was loaded. The process concludes at step 412.

Where the software determines that the user has selected a content item out of the set of content item links presented by the index page, step 406, a series of checks are executed in order to properly render the selected content item, step 416, 420, and 424. As is evident to those skilled in the art, the exact sequence in which the checks are executed is irrelevant. A check is performed to determine if the editorial content item selected by the user is a text item, step 416. If so, the presentation software renders the text data on the display device for presentation to the user, step 418. If the selected item is not a text item, step 416, another check is performed to determine if the selected editorial content item is an interactive content item, step 420. Where the selected item is an interactive content item, step 420, the application launcher is instructed to launch the application or applet capable of interpreting the interactive program code that comprises the interactive content item, step 422.

Where the software determines that the selected content item is neither a text nor an interactive editorial content item, steps 416 and 420, another check is performed to determine if the selected editorial content item is a video item, step 424. If the selected content item is a video item, the software performs an additional check to determine if video on demand (VOD) client software is installed on the set top terminal, step 426. The availability of VOD software allows the set top terminal to tune to one of the one or more dedicated or shared VOD channels operative by the service provider, step 428. The set top terminal VOD client software receives and plays back the VOD data that comprises the selected editorial content item, step 430. Alternatively, the VOD data may be delivered with the set of guide data that is periodically downloaded to the set top terminal to drive the surf guide and played back from locally stored VOD data.

The method is also applicable to set top terminals that lack VOD client software or are in use on networks where VOD functionality is not provided, step 426. Where no VOD system is in place, video data may be retrieved from an in-band communications channel which may be used to distribute guide data to set top terminals, step 432. Alternatively, the video data may be delivered along with the set of guide data that is periodically delivered to the set top terminal in order to provide data to drive the navigational surf guide. According to other embodiments, the video data may be placed on the data carousel located on the distribution network, for example at the head end, with set top terminals receiving the video data in a carousel fashion. Where check 424 returns false, the type of the selected editorial content item is identified, step 434, and the content item is rendered on the display device, step 436. When the user has concluded viewing the editorial content item, program flow returns to step 404 where the editorial content index page is presented to the user on the display device. The user is free to select additional editorial content items, step 406, or the editorial content index page may be exited, step 408.

Figure 5:
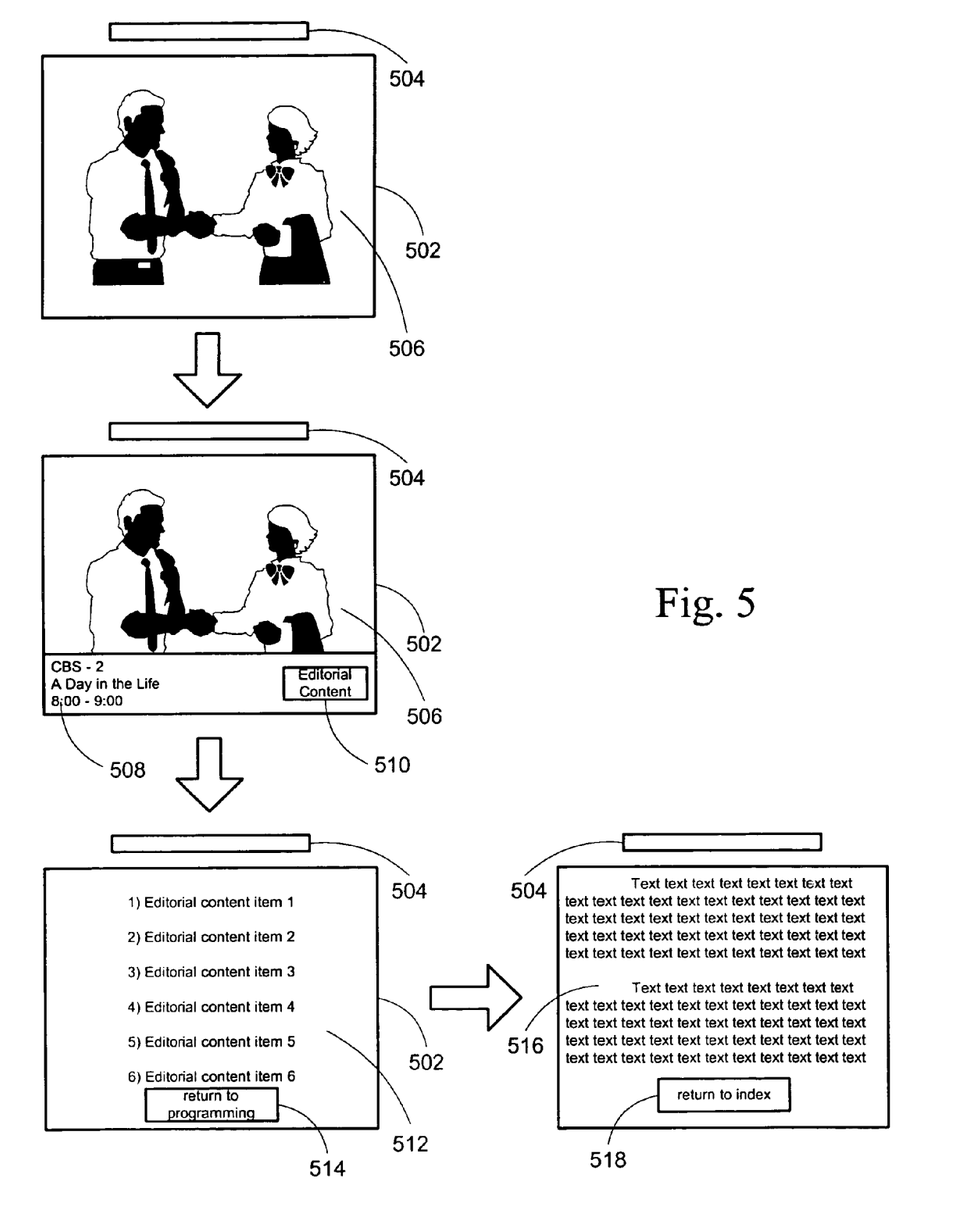
FIG. 5 is a block diagram presenting a sequence of screen shots illustrating the process of accessing editorial content.

FIG. 5 presents a sequence of block drawings of exemplary screen displays illustrating controls and content presented on a display device through use of the system and method presented in the preceding figures. The sequence starts out with programming 506, distributed by a distribution system such as a cable television provider over a distribution network, presented on a display device 502. According to this embodiment, the software components used to retrieve and present programming and editorial content is maintained in a set top terminal 504. Using an input device, such as a remote control or wireless keyboard, a user selects a control that presents the surf guide 508 on the display device 502. The surf guide is generated by the presentation software stored on the set top terminal 504 using guide data received over the distribution network, which may also be stored in the terminal 504. Also presented in the portion of the display presenting the surf guide is a graphical control 510 that allows the user to access editorial content items.

Using the input device, the user selects the graphical control 510 causing the presentation software to display an editorial content index listing the available editorial content items. The editorial content index may be stored in the terminal 504 or retrieved upon request from the distribution network, e.g., through the use of a data carousel. In response to selecting the editorial content control 510, the editorial content index page 512 is presented on the display device. In this example, the editorial content index page contains links or associations with six editorial content items 512, which may be any type of editorial content item supported by the system. Also presented on the editorial content index page 512 is a graphical control 514 that may be selected by the user to exit the editorial content index page and return to programming 506.

The user identifies an editorial content item that they wish to view and select it by manipulating the input device to select the desired item 512. The desired item is selected, causing the set top terminal 504 to display the editorial content item on the display device 516, either by retrieving it from memory or off the distribution network. In this example, the editorial content item displayed is a textual editorial content item, although other types of editorial content items are contemplated by the invention. Also provided by the presentation software is a graphical control 518 that instructs the software to remove the editorial content item from the display device and return to presenting the editorial content index 512. Upon returning to the editorial content index, the user is free to select an additional content item 512 or return to the programming 514.

While the invention has been described and illustrated in connection with preferred embodiments, many variations and modifications as will be evident to those skilled in this art may be made without departing from the spirit and scope of the invention, and the invention is thus not to be limited to the precise details of methodology or construction set forth above as such variations and modification are intended to be included within the scope of the invention.

What is claimed is:

1. A method for presenting editorial content items on a display device within the context of an electronic program guide, the electronic program guide operative to display information regarding programming available on a broadcast distribution network, the method comprising:
   receiving and storing an editorial content index page and one or more editorial content items at a client device, wherein the editorial content index page includes one or more links to the editorial content items;
   while the electronic program guide is displayed, selecting a control to present the editorial content index page on the display device;
   recovering and displaying the stored editorial content index page;
   selecting a link to an editorial content item from the set of one or more links;
   if the editorial content item of the selected link comprises a video item, determining if a video-on-demand (VOD) software is installed on the client device, tuning the client device to a video-on-demand channel if the VOD software is installed, else retrieving the video item from an in-band channel if the client device lacks the VOD software; and
   recovering and presenting the editorial content item on the display device.

2. The method of claim 1 wherein the editorial content item comprises graphics data.

3. The method of claim 1 wherein the editorial content item comprises video data.

4. The method of claim 1 wherein the editorial content item comprises interactive program code and wherein presenting the editorial content comprises executing the interactive program code.

5. The method of claim 4 wherein the interactive program code enables a client device to interact with a remote program code and data.

6. The method of claim 1 wherein presenting the editorial content item on the display device comprises:
   determining a type of the editorial content item;
   selecting a rendering program based on the type of the editorial content item; and
   executing the rendering program to present the editorial content item on the display device.

7. A method for presenting editorial content items on a display device, the method comprising:
   receiving and storing an editorial content index page and one or more editorial content items at a client device, wherein the editorial content index page includes one or more pointers to the editorial content items;
   presenting an electronic program guide operative to display information regarding programming available on a broadcast distribution network and a selectable editorial content control within the electronic program guide to present an the stored editorial content index page;
   presenting the stored editorial content index page on the display device within the context of the electronic program guide in response to a selection of the editorial content control;
   selecting a pointer to an editorial content item;
   if the editorial content item of the selected pointer comprises a video item, determining if a video-on-demand (VOD) software is installed on the client device, tuning the client device to a video-on-demand channel if the VOD software is installed, else retrieving the video item from an in-band channel if the client device lacks the VOD software; and
   recovering and presenting the editorial content item on the display device.

8. The method of claim 7 receiving the editorial content index page and one or more editorial content items is performed on a periodic basis.

9. The method of claim 7 comprising receiving the editorial content index page and one or more editorial content items at a client device through a carousel distribution system distributing the editorial content index page and one or more editorial content items in a carousel fashion.

10. The method of claim 7 comprising:
    exiting the editorial content index page; and
    presenting the electronic program guide and editorial content control upon exiting the editorial content index page.

11. The method of claim 7 comprising:
    exiting the editorial content index page; and
    presenting a channel displayed on the display device when the step of presenting the electronic program guide is executed.

12. A method for presenting editorial content items on a display device, the method comprising:
    presenting a surf guide configured to display program information concurrently with a tuned channel and with a selectable editorial content control to present an editorial content index page;

receiving and storing editorial content items and an editorial content index page having pointers to the editorial content items;

presenting the editorial content index page on the display device within the context of the surf guide in response to a selection of the editorial content control;

selecting a pointer to an editorial content item from the set of one or more pointers;

if the editorial content item of the selected pointer comprises a video item, determining if a video-on-demand (VOD) software is installed on a set top terminal (STT), tuning to a video-on-demand channel if the VOD software is installed, else retrieving the video item from an in-band channel if the STT lacks the VOD software; and presenting the editorial content item on the display device.

13. The method of claim 12 comprising:
exiting the editorial content index page; and
presenting the surf guide and the editorial content control upon exiting the editorial content index page.

14. The method of claim 12 comprising:
exiting the editorial content index page; and
presenting a channel displayed on the display device when the step of presenting the editorial content index page is executed.

15. Computer readable media comprising program code, the program code capable of being executed by a microprocessor, the program code comprising a method for presenting editorial content items on a display device, the method comprising:

presenting an electronic program guide operative to display information regarding programming available on a broadcast distribution network and a selectable editorial content control within the electronic program guide to present an editorial content index page;

receiving and storing editorial content items and an editorial content index page having pointers to the editorial content items;

presenting the editorial content index page on the display device within the context of the electric program guide in response to a selection of the editorial content control;

selecting a pointer to an editorial content item from the set of one or more pointers;

if the editorial content item of the selected pointer comprises a video item, determining if a video-on-demand (VOD) software is installed on a set top terminal (STT), tuning to a video-on-demand channel if the VOD software is installed, else retrieving the video item from an in-band channel if the STT lacks the VOD software; and presenting the editorial content item on the display device.

16. A system for presenting editorial content items on a display device, the system comprising:

one or more received and stored editorial content items comprising, audio, video, and interactive data and combinations thereof;

a received and stored editorial content index page comprising a set of pointers to the stored one or more editorial content items; and presentation software operative to generate and present on a display device navigational controls and an electronic program guide, the presentation software further operative to display the editorial content index within the context of the electronic program guide and render the editorial content index page and one or more editorial content items on the display device in response to a selected user command, wherein if the one or more editorial content items selected comprises a video item, video-on-demand (VOD) client software operatively renders video data if the VOD client software is installed, else retrieving the video item from an in-band channel if the VOD client software is not installed.

* * * * *